United States Patent [19]

Hettich

[11] Patent Number: 4,773,418
[45] Date of Patent: Sep. 27, 1988

[54] METHOD FOR MANUFACTURING A TRANSPLANT

[76] Inventor: Rolf Hettich, Bohnenberger Strasse 5, D-7400 Tübingen, Fed. Rep. of Germany

[21] Appl. No.: 946,073

[22] Filed: Dec. 24, 1986

Related U.S. Application Data

[63] Continuation of Ser. No. 644,718, Aug. 22, 1984, abandoned.

[30] Foreign Application Priority Data

Dec. 22, 1982 [DE] Fed. Rep. of Germany ....... 3247387
Dec. 9, 1983 [WO] PCT Int'l Appl. ...PCT/EP83/00329

[51] Int. Cl.$^4$ ............................................. A61F 17/32
[52] U.S. Cl. .................................... 128/305.5; 600/36
[58] Field of Search .................... 128/1 R, 305.5, 305, 128/DIG. 1

[56] References Cited

U.S. PATENT DOCUMENTS

| | | | |
|---|---|---|---|
| 3,076,461 | 2/1963 | Meek et al. .......................... | 128/305 |
| 3,257,884 | 6/1966 | Best et al. .......................... | 128/305.5 |
| 3,327,711 | 6/1967 | Vallis ................................. | 128/305.5 |
| 3,358,688 | 12/1967 | Tanner ............................... | 128/305.5 |
| 3,412,732 | 11/1968 | Simon ................................ | 128/305.5 |
| 3,472,228 | 10/1969 | Tanner ............................... | 128/305.5 |
| 3,613,242 | 10/1971 | Hill et al. .......................... | 128/305.5 |
| 3,640,279 | 2/1972 | Brown et al. ...................... | 128/305.5 |
| 4,304,866 | 12/1981 | Green et al. ...................... | 128/305.5 |

FOREIGN PATENT DOCUMENTS 1267784 5/1968 Fed. Rep. of Germany ...... 128/305

OTHER PUBLICATIONS

Plastic and Reconstructive Surgery, Aug. 1982, C. C. Yang et al. "A Chinese Concept of Treatment of Extensive Third-Degree Burns", pp. 238-252.

*Primary Examiner*—John Weiss
*Attorney, Agent, or Firm*—John F. Witherspoon

[57] ABSTRACT

A method and apparatus for producing a graft for a patient consisting of foreign skin provided with openings and segments of a piece of the patient's original skin inserted into the openings are disclosed. A piece of the patient's original skin is cut into segments arranged at specific locations in a system of coordinates. A backing, carrying foreign skin, is also placed within the system of co-ordinates and openings are cut into the foreign skin at similarly defined locations. The segments of the patient's original skin are then placed by mechanical means into the openings of the foreign skin.

9 Claims, 7 Drawing Sheets

METHOD FOR MANUFACTURING A TRANSPLANT

This is a continuation of application Ser. No. 644,718 filed Aug. 22, 1984 abandoned on 1/3/87.

DESCRIPTION

The invention relates to a method for manufacturing a transplant, consisting of foreign skin provided with openings and small pieces of the patient's own skin inserted into the openings.

In cases of severe burns there is the problem of covering the injury, inasmuch as often only very small areas of original skin (for example the head) remain intact for removal of a graft. However, final covering of skin injuries with foreign skin or skin substitute foil alone has not so far been possible. Thus the patient's own available skin must be used as economically as possible. The remaining healthy original skin is removed in stages so as gradually to supply the burned areas with grafts.

It is known that it is not necessary to cover all surfaces damaged by burning with original skin. It is sufficient to cover the areas damaged by burns with foreign tissue, for example with cadaver skin, and to implant islands of original skin only at certain intervals. From these islands endogenous epithelial cells grow over the exogenous corium of synthetic corium-substitute foil, thus forming a definitive, cosmetically functional and entirely satisfactory closure of the burn injury. See Yang Chih-chun, Shih Tsi-siang, and Xu Wei-shia, A Chinese Concept of Treatment of Extensive Third-Degree Burns, PLASTIC AND RECONSTRUCTIVE SURGERY, August 1982, pp. 238-252.

Until the present, small round openings were laboriously cut by hand into pieces of cadaver skin, after which corresponding pieces of original skin were inserted into them. This is extremely time-consuming. Even with a group of several operators, several hours are required to create the graft consisting of foreign skin and implanted original skin, for instance to cover a single area.

It is the purpose of this invention to accelerate and simplify this method.

It is possible by this invention to cut very rapidly precisely defined square (for example) pieces of original skin and to cut corresponding square openings into the cadaver skin and to insert these pieces of original skin into these openings. This need not necessarily take place on the operating table. It is possible to carry out the preparation of these grafts in a separate method in the laboratory, as soon as the necessary original skin is available.

The method and the equipment described are particularly expedient because human skin is extremely tough and difficult to handle. Small pieces of skin are especially hard to manipulate with tweezers, among other things because skin has a tendency to roll up and to adhere to any kind of manipulating instrument (for example tweezers), and the like.

The invention further ensures 100% utilization of the remaining original skin. "Foreign" skin consists of cadaver skin, parts of animal skin and skin-substitute preparations on a synthetic base.

Examples of the invention with the advantageous new advances made therein will be described below, with reference to the attached drawings, wherein.

Figure 1:
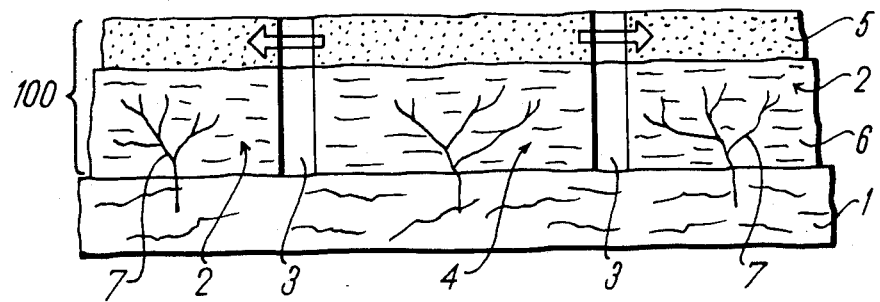
FIG. 1 is a cross-section through a graft.
Figure 2:
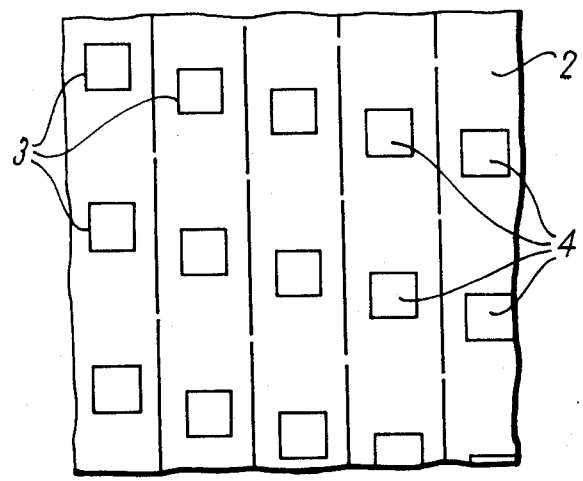
FIG. 2 is a plan view of the cadaver skin prepared for production of a graft.

According to FIG. 1, in the course of a skin graft a graft is placed on intact tissue 1. Since in many cases not as much of the patient's own skin is available as would be desirable, as in the case of extensive burns, large pieces of foreign skin 2 (FIG. 2) are used and tissue 1 is covered therewith. Openings 3 are provided in foreign skin 2, into which small pieces of original skin are inserted.

In much simplified terms, skin consists of epithelium or epidermis 5 (outer skin) and corium 6 (dermis). Because of its high antigen content (the stimulation index of a mixed epitheliumlymphocyte culture is about 500 times as high as that of a mixed fibroplastic lymphocyte culture corresponding to the component parts of the corium of foreign skin), the epithelium 5 is very quickly recognized by the immune system as foreign tissue and rejected; simultaneously, the epithelium 6 of the original skin 4 grows onto the corium of the foreign skin 2 in the direction of the arrows; meanwhile vessels 7 from tne intact tissue 1 grow into the corium 6. This is referred to as a "sandwich phenomenon", meaning that after epithelium 5 of cadaver skin 2 has been replaced by the new epithelium grown from original skin 4, the foreign corium lies between the newly formed original epithelium and intact tissue, until it is gradually reabsorbed and replaced by the body's own tissue.

A grafting procedure of this kind is extermely time-consuming. The main reason is that the natural properties of skin make it very difficult to handle. It is extremely resistant and thus it is very difficult to cut accurately. In addition, pieces of skin such as those removed from healthy parts of the body by means of a dermatome for the transplantation are difficult to manipulate, since they roll up and stick together, or to instruments such as tweezers. Even for a term of several operators, the procedure described above is extremely time-consuming. On the other hand in the case of extremely severe burns this is the only way to cover the necessary areas if only a small amount of healthy original skin remains.

Figure 5:
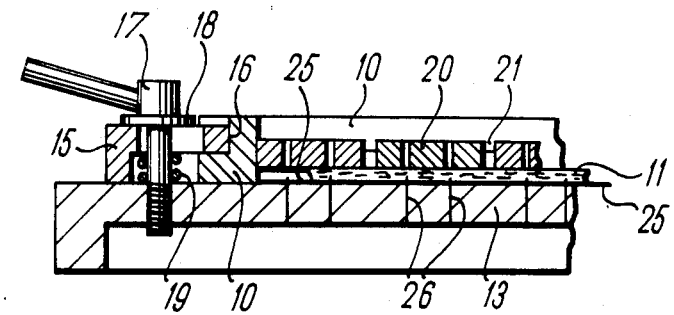
FIG. 5 is a cross-section along the line V—V in FIG. 3.
Figure 6:
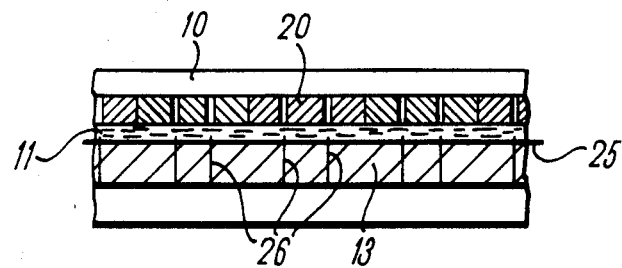
FIG. 6 is a cross-section along the line VI—VI in FIG. 3
Figure 7:
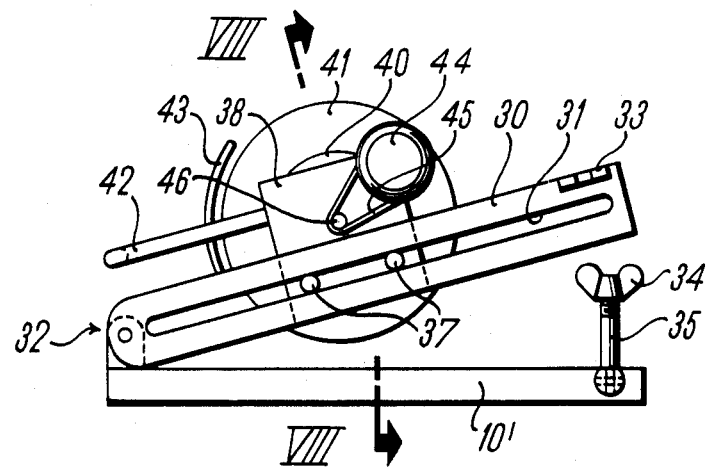
FIG. 7 shows a modification of the cutting device according to FIGS. 3 to 6.
Figure 8:
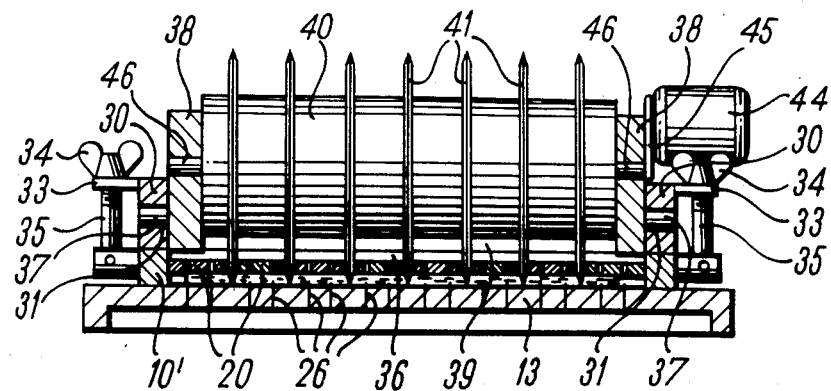
FIG. 8 is a cross-section along the line VIII—VIII in FIG. 7.

The method according to the invention and the devices pertaining thereto greatly simplify the procedure. A description will first be given of the individual pieces of equipment:

Cutting frame 10, as shown in FIGS. 3 to 6 and in a modification shown in FIGS. 7 and 8, serves to cut original skin 11 into small rectangular, preferably square pieces. These pieces of original skin then correspond to original skin 4 according to FIG. 1.

Cutting frame 10 is devised with the external dimensions of a square, so that it can be used in two positions rotated through 90° in relation to each other (see FIGS. 3 and 4), between positioning block 12 on baseplate 13. A piece of original skin 11, which is to be cut into pieces, is placed between the cutting frame 10 and baseplate 13. The cutting frame is secured to the baseplate by means of clamping devices 14, each consisting of an L-shaped angle piece 15, as shown in FIG. 5, disposed in a recess 16 in the cutting frame 10, of a locking screw 17 with a pressure collar 18, and a spring 19 which pushes the angle piece 15 upwards. Clamping devices 14 and positioning block 12 allow the cutting frame to be brought to an accurately defined position over original skin 11 and to be locked in that position; the piece 11 is now securely clamped between the cutting frame and the baseplate.

Figure 3:
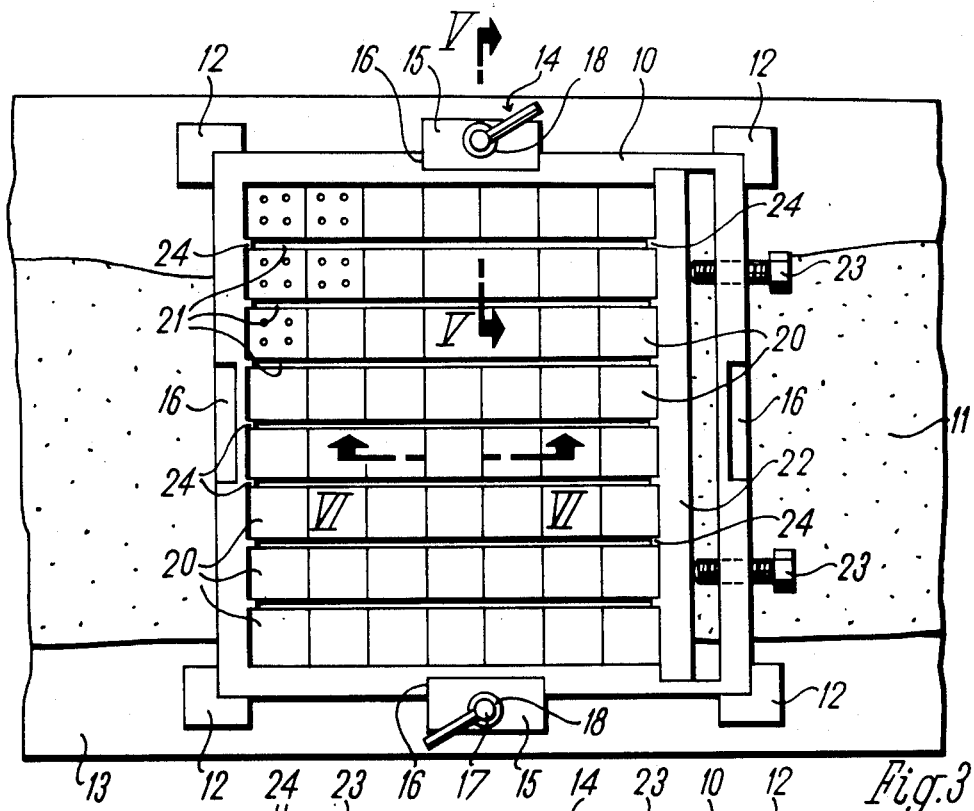
FIG. 3 is a device ror cutting original skin.

Square metal plates 20 are now clamped in rows in cutting frame 10 in such a manner as to leave spaces 21 between these rows, thus allowing the piece of original skin 11 to be cut into strips. In FIG. 3 these spaces run horizontally, and in FIG. 4—after a 90° rotation of cutting frame 10 including the metal plates clamped thereto—they run vertically. Along the spaces 21 the original skin 11 can be sliced first horizontally (FIG. 3) and then vertically (FIG. 4), thus producing square segments 4 of original skin.

Figure 4:
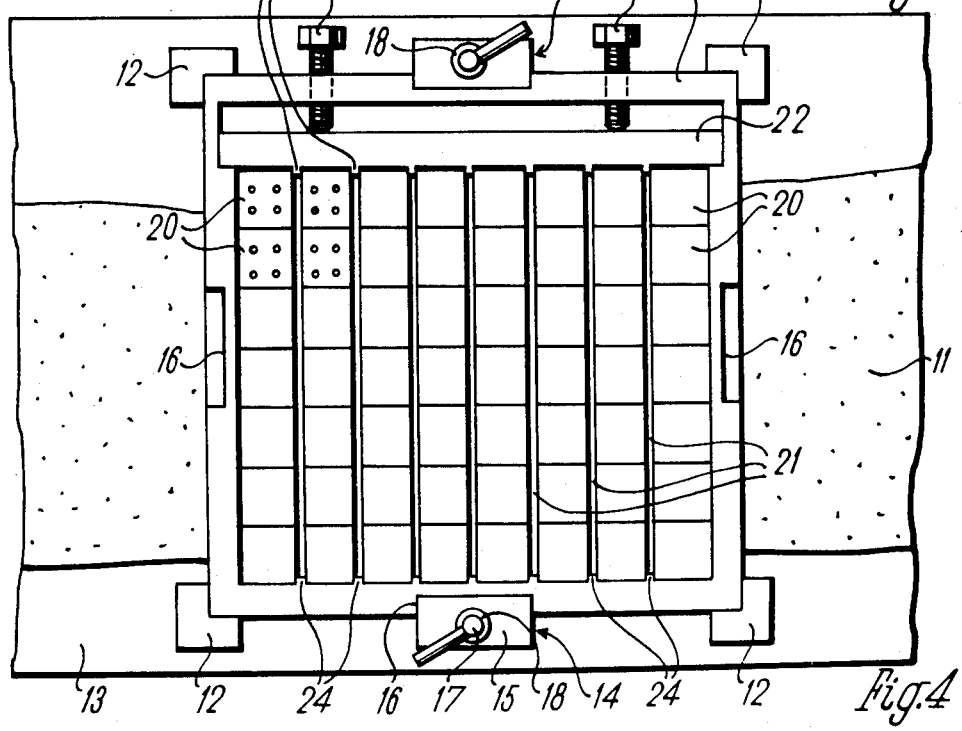
FIG. 4 is the device in FIG. 3 rotated by 90°.

For metal plates 20 to be clamped to the cutting frame as shown, a clamping strip 22 is arranged in the cutting frame 10 on the right-hand side of FIG. 3, and at the top of FIG. 4, the clamping strip being movable and pressed against metal plates 20 by means of screws 23 in threaded holes in cutting frame 10. Alternatively an eccentric clamping lever may hold clamping element 22 at several points in the desired compressed position.

The arrangement of metal plates 20 in the frame in rows, in such a manner as to produce, spaces 21, is facilitated by projections 24 on cutting frame 10 and on clamping element 22. Metal plates 20 are inserted and clamped into position by tightening screws 23 on a flat base. To ensure that the plates are in alignment, and the spaces 21 are therefore straight, spacers may be inserted, the spacers being removed after the plates have been clamped in position. The use of preformed plastic templates is also possible.

First, cutting frame 10 is therefore clamped in the manner shown in FIG. 3. Next, a piece of original skin 11 is cut along spaces 21. Clamping devices 14 are then released, the frame is rotated through 90°, is reinserted and the clamping devices are tightened again. The vertical cuts are now made along spaces 21, as shown in FIG. 4. Original skin 11 is thus cut into numerous square segments 4.

The metal plates 20 have an edge length of 5-10 mm, for example. The square pieces of original skin are of a corresponding size. The edge length of the cutting frame may be between 25 and 30 cm and may be used for plates 20 of various sizes with different clamping elements 22.

As may be seen from FIGS. 5 and 6, a cutting foil 25 is placed under the piece of original skin 11. This allows the skin to be cut completely through with a smooth edge, without the scalpel or other cutting instrument used for the purpose being pressed directly against the metal of baseplate 13.

As as may be seen from FIGS. 5 and 6, steel pins 26 are inserted into baseplate 13 at intervals of 2-3 mm. This is devised so that the pins project from the upper surface of baseplate 13 far enough that they just penetrate through cutting foil 25 and with the tips projecting by 0.1-0.2 mm from the cutting foil they penetrate into the surface of the skin 11 and secure it to the baseplate 13, so that it cannot be moved; by this means it is possible to avoid segments 4 rolling up again or assuming an undesirable position while being cut and after being removed from cutting frame 10 (see below). The tips of the steel pins 26 just barely penetrate into the surface of original skin 11 that lies up against cutting foil 25. Original skin 11 is about 0.5-0.7 mm thick.

It is, of course, also possible to achieve securing of the piece of original skin to the surface of baseplate 13, or to cutting foil 25, by other means, for example by providing the surface of the foil with projections or other means of gripping. It would also be conceivable to glue the skin to baseplate 13, possibly with glues tolerated by the body. In this case, however, the skin would have to be released again after cutting.

Cutting of the original skin 11 can be achieved simply when it is clamped in the cutting frame, by means of a scalpel. This can be further simplified, however, using the modification shown in FIGS. 7 and 8: In FIGS. 7 and 8 two cutting roller guides 30 swing upward on cutting frame 10'. They are devised in the form of elongated rails with guide slots 31 and are secured to one side of cutting frame 10' by means of a hinge 32. On the other side, cutting roller guides 30 may be secured by formed hooks 33, wing-nuts 34 and threaded bolts 35 hinged to cutting frame 10'. The two cutting roller guides in conjunction with backplate 36 constitute a frame which can be swung upwards.

Running in guide slots 31 of cutting roller guides 30 are guide pins 37, each fitted to a plate 38. Plates 38 form a frame for a cutter roller 40 in conjunction with backplate 39. On cutting roller 40, cutting wheels 41 are arranged at intervals equal to the distance between spaces 21 in FIGS. 3 and 4. On the frame formed by plates 38 and backplate 39 there is also a handle 42 which serves to pull the frame with cutter roller 40 from one end of guide slots 31 to the other (in other words from right to left in FIG. 7). A protective plate 43 fitted to the handle protects the user's hand. Cutter roller 40, with cutting wheels 41, is driven by a motor 44 by means of a belt 45 and a shaft 46 secured to cutter roller 40. Cutting roller 40 may consist of several cylindrical sections alternating with cutting wheels 41, all mounted on shaft 46, resulting in the structure shown in FIG. 8. The diameter of cutting wheels 41 is such that when cutting frame 10', to which the cutter roller guides are secured, is clamped to baseplate 13, the cutting wheels cut directly into foil 5, thus ensuring that original skin 11 is definitely cut through.

For the purpose of cutting through original skin 11, it is possible to use, instead of motor-driven cutting wheels which are moved manually along the cuts, other mechanical means, for example a punch, or the like, adapted to move up and down.

Upon completion of the cutting process as indicated in FIGS. 3 to 8, the piece of original skin 11 is in the form of square segments 4 which are still clamped (see FIG. 4) between metal plates 20 and baseplate 13. Further handling now takes place as described hereinafter.

Figure 9:
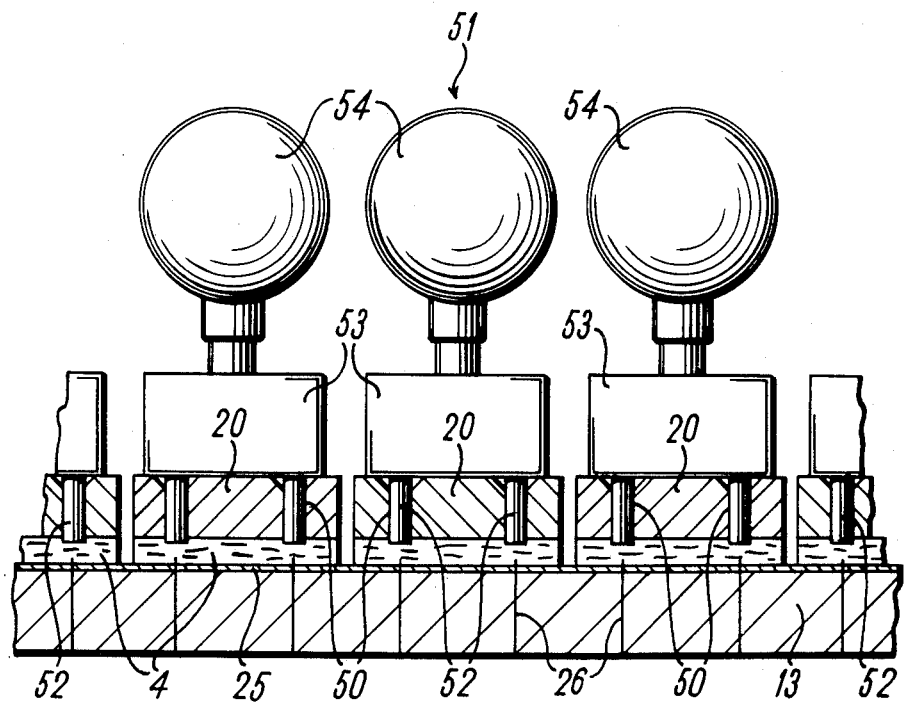
FIG. 9 is a cross-section through the small plates 20 used in the cutting device according to FIGS. 3 to 6, with a transporting attachment 51 placed thereon.

In the embodiment illustrated, metal plates 20 are provided with four cylindrical openings 50, as shown in FIG. 9. This makes it possible to place pressure/section units 51 upon the metal plates after the skin has been cut. These are known broadly as "transporting attachments" and are used to lift segments of skin 4, together with metal plates 20, from baseplate 13 and to insert them into openings 3 in cadaver skin 2 (see FIG. 2).

In the embodiment illustrated, the transporting attachment consists of four tubes 52 which pass through openings 50 in each metal plate 20. The upper ends of openings 50 are flared to facilitate introduction of the tubes. During transportation, the lower ends of tubes 52 are sealed to metal plates 20. However, when the segments of skin are set down, the tubes project slightly in order to release the skin from plates 20. The upper ends of the tubes communicate with a chamber 53 which, in turn, communicates with a compressible rubber ball 54.

After the cuts have been made, a transporting attachment 51 of this kind must be placed upon each metal plate 20 and the rubber ball must be compressed. The resulting negative pressure in tube 52 ensures that when the transporting attachment is lifted from baseplate 13, segments of skin 4 will also be lifted and will not remain attached to baseplate 13. Thus, when the transporting attachment is lifted, metal plate 20 and segment 4 thereunder are also lifted. Because of the extremely light weight of such a segment 4 of skin, the negative pressure applied to the skin through tubes 52 need only be minimal. This force is also sufficient to release segments 4 of original skin from the tips of steel pins 26 projecting from the surface of baseplate 13 since, because of the elasticity of the skin, the tips do not penetrate into the skin but act merely like claws to prevent the skin from moving on the baseplate. It is possible to arrange for tubes 52 to have no play in passages 50, so that metal plates 20 are held to the transporting attachments by friction between tubes 52 and passages 50.

Figure 12:
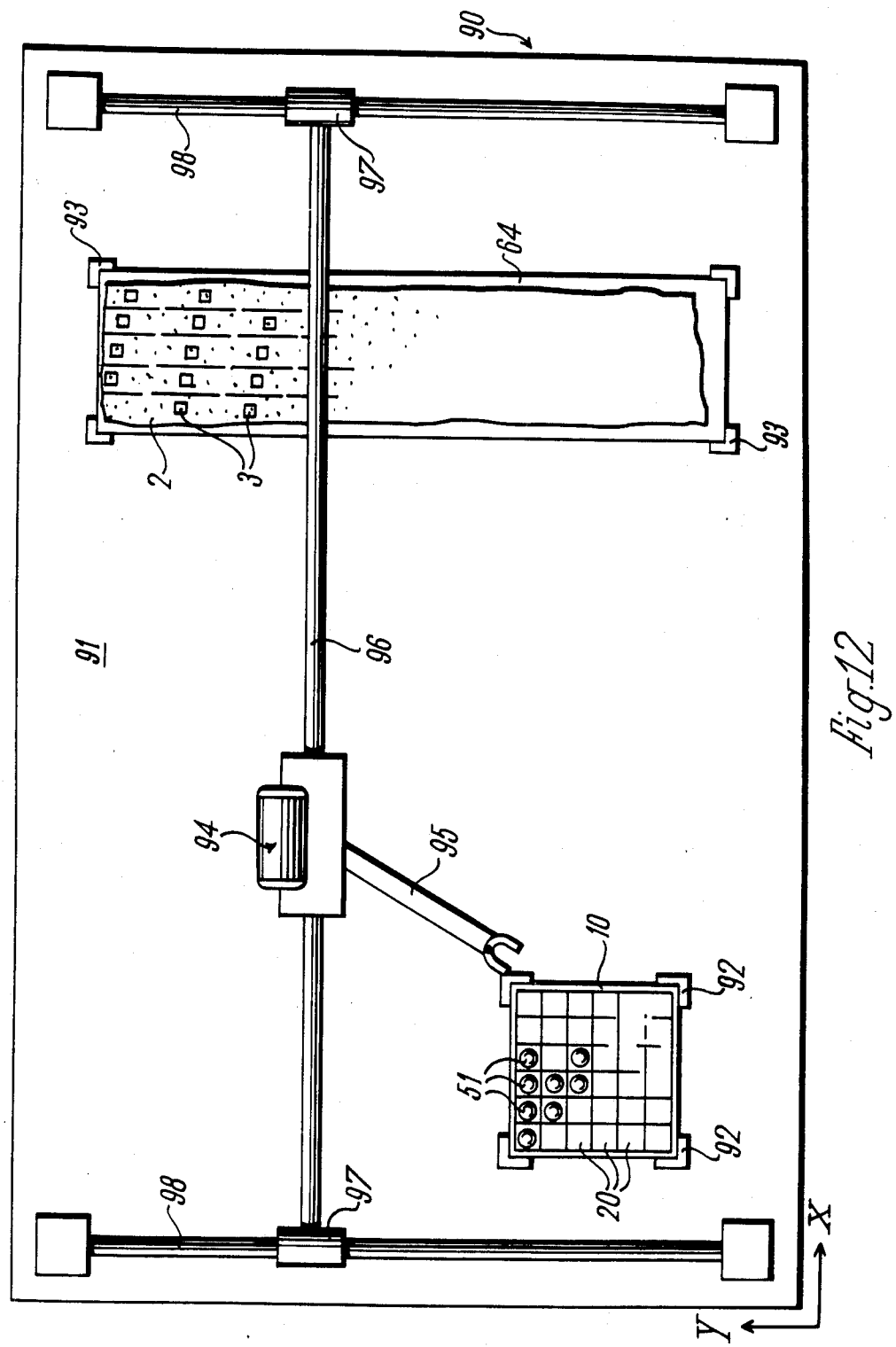
FIG. 12 is a plan view of a transfer device.

As soon as transporting attachments have been placed on each of metal plates 20, the cutting frame 10, together with metal plates 20, transporting attachments 51, and underlying segments 4 are brought to the transfer device 90 (see FIG. 12). Screws 23 in cutting frame 10 are then released, so that the transporting attachments, together with metal plates 20 and segments 4, can then be handled separately and may thus be inserted into opening 3 in foreign skin 2.

Rubber ball 54 may also be replaced by other means designed to produce negative and positive pressure in tubes 52. Since the pressure differences needed are quite small, the lines may be fine enough not to be in the way. The changeover from positive to negative pressure, and vice-versa, may be effected by means of valves.

Figure 10:
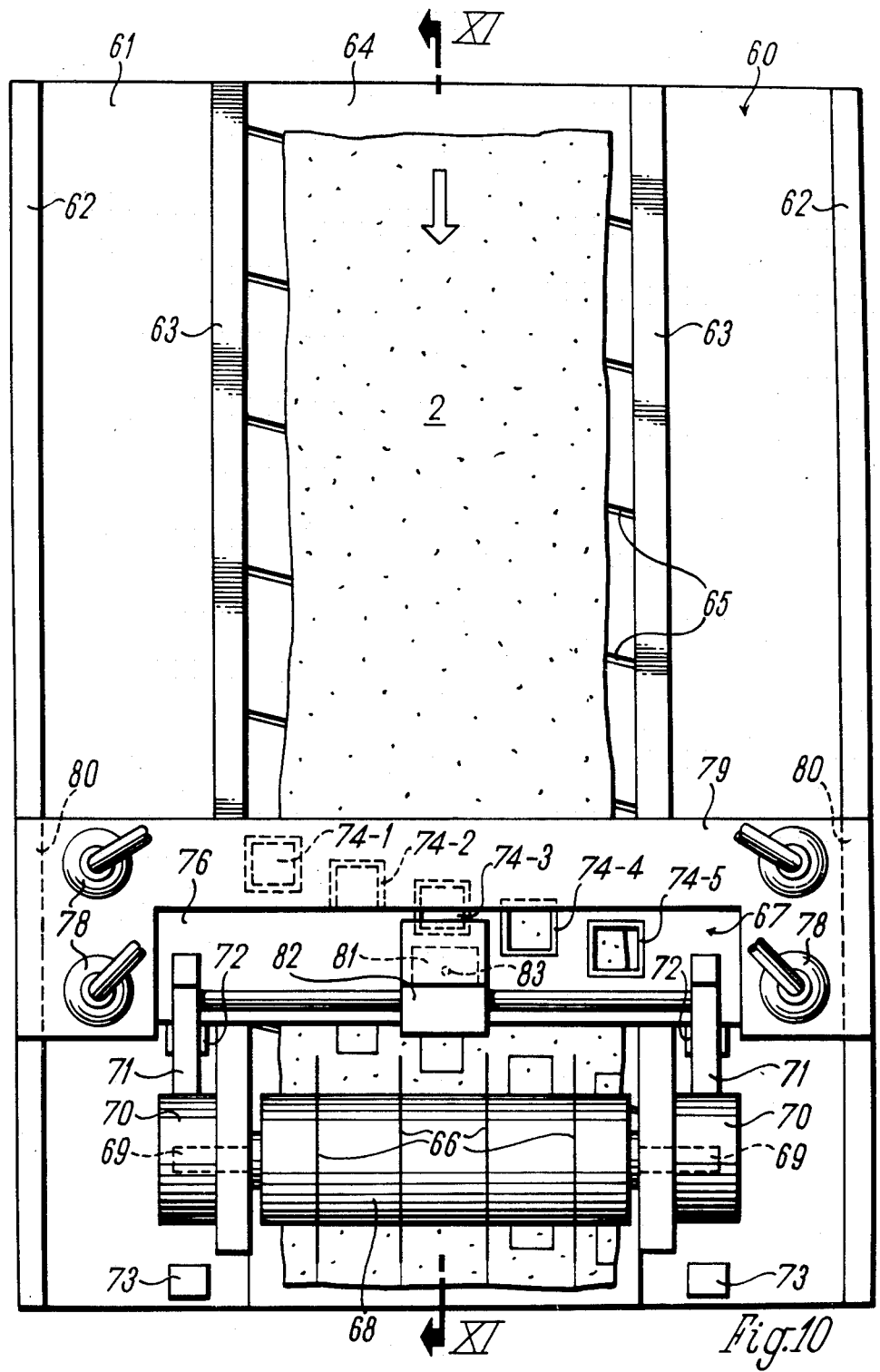
FIG. 10 is a plan view of a punching device for punching openings in the cadaver skin.
Figure 11:
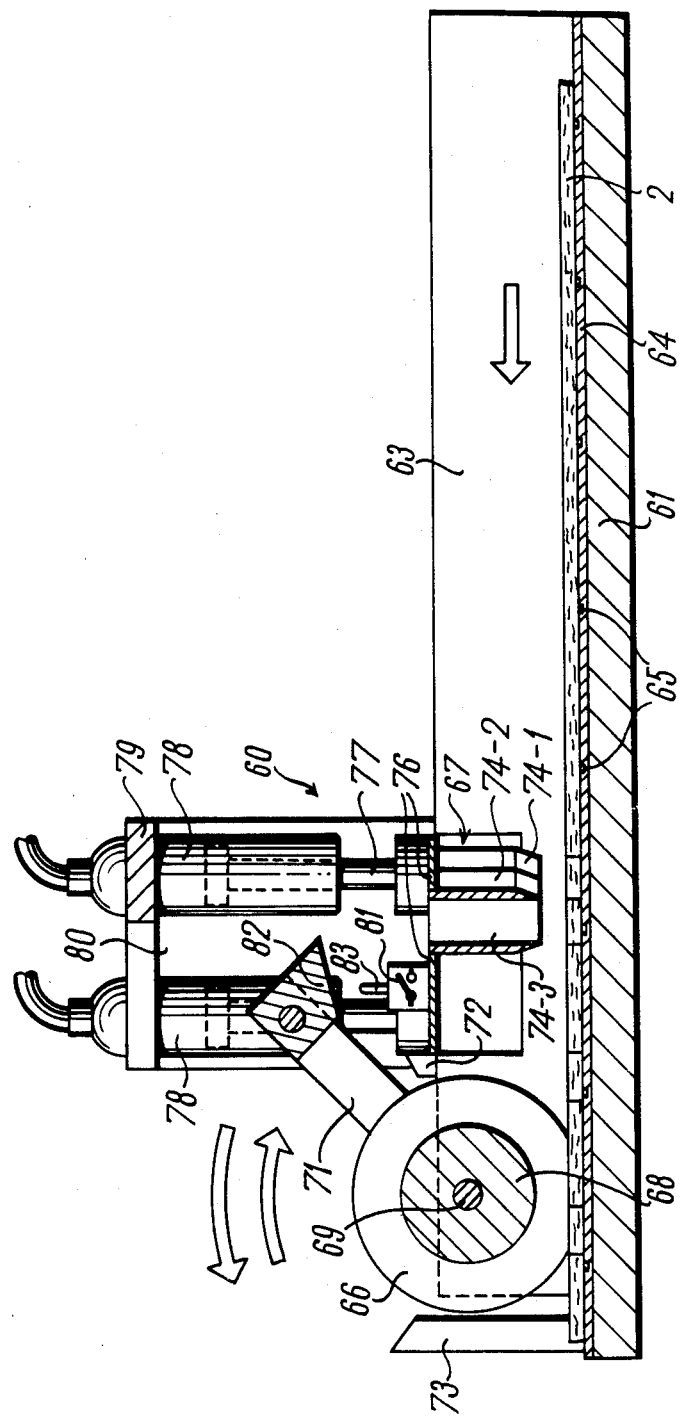
FIG. 11 is a cross-section along the line XI—XI in FIG. 10.

Foreign skin 2 is prepared for the insertion of segments 4 of original skin as shown in FIG. 12 by means of a punching device 60 shown in FIGS. 10 and 11 and comprising a baseplate 61, two lateral plates 62 and two guide rails 63. Foreign skin 2 is placed between the guide rails, upon a piece of transporting and cutting foil 64 provided, in a manner known per se, with grooves running at an angle to the direction ot transportation. The distance between the grooves is such that a row of openings 3 can be punched between each pair of grooves. If foreign skin 2 is now passed under cutters 66, the latter cur through the skin in the areas where the foreign skin rests, between grooves 65, flatly upon transporting and cutting foil 64. Where grooves 65 are below foreign skin 2, the skin can escape into the grooves before the cut. Thus uncut webs are left above the grooves between the cuts, and these hold the skin together. The cuts thus made allow secretions, formed between the cadaver skin and the tissue, to flow away after transplantation. Although this is known per se, the use thereof in the present context is particularly useful.

As may be gathered from FIGS. 10 and 11, transporting and cutting foil 64 is passed in the direction of transportation (see arrow) beneath a punching unit 67. A transporting and cutting roller 68, in which cutters 66 are arranged, is used to cut the skin while punching unit 67 provides it cyclically with punched openings 3, and advances it over accurately defined distances.

Transporting and cutting roller 68 is connected rigidly to a shaft 69 mounted at both ends in guide rails 63 and connected, through a free-wheel hub 70, to a hand lever 71. The connection between hub 70 and the shaft 69 is sucn that if hand lever 71 is moved in a clockwise direction (as shown by the lower arrow to the left of FIG. 11) until it reaches a stop 72, the shaft, and with it transporting and cutting roller 68, rotates with the hand lever; thus transporting and cutting foil 64 is drawn, together with foreign skin 2, between transporting and cutting roller 68 and baseplate 61 and is advanced over an accurately defined distance. The hand lever is then moved back in a counter-clockwise direction (as shown by the upper arrow to the left of FIG. 11) until it reaches stop 73. During this counter-clockwise movement, shaft 69 does not move with hand lever 71, but continues to rotate freely. A coupling of this kind, engaging in one direction only, is known per se and requires no further explanation.

During the transporting movement in which the foreign skin is cut, as shown in FIG. 10, in the manner already indicated, the foreign skin passes under punching unit 67. This unit comprises, at an angle to the transporting direction and parallel with grooves 65, five punching tools 74-1 to 74-5 all of which are square and have cutting edges at the bottom. When these punches move down onto the foreign skin, square holes 3 are cut out in the configuration illustrated in FIG. 12. The punching tools are secured to plate 76 engaging with four pistons 77 running in cylinders 78. The latter are secured to a header 79 retained by two lateral plates 80 secured to the abovementioned lateral plates 62. When pressure is applied to pistons 77 in cylinder 78, plate 76 with punches 74-1 to 74-5 travels downwardly and punches a row of openings 3 out of foreign skin 2.

The punching operation is synchronized with the transporting operation in that an electrical switch 81 is arranged on punch plate 76, the switch being actuated as soon as stop 82, arranged upon hand lever 71, strikes contact pin 83 on switch 81. This occurs at the end of each advancing cycle which is defined as the clockwise movement of hand lever 71 until it reaches stop 72. Punching tool 67 (comprising punch plate 76 and punches 74-1 to 74-5) then moves downwardly, punches out the holes, and then moves back upwardly. The hand lever is then returned.

As may be gathered from FIG. 10, header 79 is U-shaped in plan view, so that it is easy to grasp with the hand transverse rod 84 which is a part of hand lever 71 and carries stop 83.

As soon as transporting and cutting foil 64, carrying foreign skin 2, has passed completely through punching device 60, it is placed, with the skin now cut, in transfer device 90, as shown in FIG. 12.

The transfer device consists of a plate 91 upon which is arranged a first positioning block 92 for the accommodation of cutting frame 10 (or 10') and a second positioning block 93 for the accommodation of the transporting and cutting foil carrying foreign skin 2. Manipulator 94, comprising a mobile gripper 95 and moving in an x/y system of coordinates, takes up individual transporting attachments 51 with dependent plates 20 and segments 4 of original skin, after screws 23 have been released, and inserts them consecutively into openings 3 in foreign skin 2. Manipulator 94 is displaceable upon rod 96 in the x-direction, while rod 96, with sleeves 97, is displaceable upon rod 98 in the y-direction. Programmable manipulators of this kind are available commercially and it is therefore unnecessary to describe them in greater detail in this context. It must be borne in mind that the position of each transporting attachment within cutting frame 10, and that of openings 3 in transporting and cutting foil 64, is accurately defined because of the prior mechanical processing steps. Manipulator 94 can therefore be programmed to insert one transporting attachment 51 after the other into an opening 3. It is also possible to control these insertions, without accurate coordination of the openings, by means of sensors operating with light scanners or the like.

Cadaver skin 2 is thus prepared with segments 4 of original skin and the whole graft, consisting or cadaver skin 2 with inserted segments 4 of original skin, can be transplanted by an operator.

Transfer device 90 may also be of a different design. A simplified device comprises positioning blocks on one side for cutting frame 10 and, on the other side, for transporting and cutting foil 64, in which these parts may be placed. According to one semi-mechanical design, transporting attachments 51 may also be transferred by hand into individual openings 3 in cadaver skin 2.

After all of the segments have been inserted by transfer device 90 into foreign skin 2, the resulting graft is glued to a piece of foil which ensures that the graft retains its shape upon being removed from backing 64 and also that the segments of original skin remain in the openings in the foreign skin. This is the form in which the graft is brought to the part of the patient which is to be covered.

The devices and the method described hereinbefore thus make it possible to separate the production of a graft both spatially and chronologically from the actual grafting operation; it would be conceivable to make the devices described mobile (mounting them in special vehicles or the like) and to move them, together with a crew trained to operate them, for a short time, to the location where they are needed, for example to a hospital where a patient with severe burns is being cared for.

In one embodiment, it is assumed that transporting attachments 51 form, together with metal plates 20, "transporting parts", i.e., elements which make it possible to insert the segments of original skin, cut into squares in the frame, into openings 3 in foreign skin 2, the transporting attachments being picked up by gripper 95 described in conjunction with FIG. 12. It is also possible to modify this device in such a manner as to provide, on manipulator 94 or at the end of gripper 95, special means—for example a pair of tongs with a stripper—to seize plates 20 with the underlying segments, to insert the latter into openings 3 in foreign skin 2 and to release or strip them there. It would then be unnecessary for the number of transporting attachments to equal the number of segments; instead, a single device would suffice.

In the case of the transporting attachment according to FIG. 9, provision is made for four tubes 50 to pass downwardly through openings in metal plates 20, suction being applied to the segments 4 of original skin, through these tubes, during lifting and pressure being applied during releasing. It is also possible to provide a larger number of small tubes in order to prevent the segments from adhering to the bottom surface of the plates. In this case, simple strippers or the like means could be provided.

Many variations of the above described method and apparatus which do not depart from the spirit and scope of the invention will be readily apparent to persons skilled in the art.

What is claimed is:

1. A method for producing a graft for a patient wherein foreign skin is provided with openings and segments of a piece of the patient's original skin are inserted into said openings, which method comprises placing a holding device in a transfer device at a location within a system of coordinates having segments of the patient's original skin arranged therein at specific locations; placing a backing, carrying foreign skin, at another location within said system of coordinates; cutting openings into the foreign skin at defined locations; placing a transporting device on each segment of the patient's original skin, said transporting device comprising means which, upon being lifted, carry along segments of the patient's original skin and, upon being set down, release said segments; and moving said transporting device to said openings in said foreign skin and placing said segments of original skin therein.

2. A method as defined in claim 1 wherein said foreign skin is cadaver skin, parts of animal skin, synthetic skin substitute, or some other skin substitute preparation.

3. A method as defined in claim 1 wherein secretion discharge slots are cut into the foreign skin.

4. A method as defined in claim 1 wherein said segments of original skin are polygonal.

5. A method as defined in claim 4, which further comprises arranging and clamping square platelets in rows in said holding device in such a manner as to form spaces between said rows; placing a piece of said original skin on a backing member; placing said holding device and clamped-in platelets on said original skin and backing member in a first position; cutting said piece of original skin along said spaces; removing said holding device and clamped platelets from said piece of original skin and rotating same through 90 degrees; again placing said holding device and platelets upon said original skin; and again cutting said piece of original skin along said spaces to thereby cut said piece into square segments.

6. A method as defined in claim 5, which further comprises placing transporting attachments upon said platelets after said original skin has been cut twice and thereby forming with said platelets a transporting device for moving said segments.

7. A method for producing a graft for a patient wherein foreign skin is provided with openings and segments of a piece of the patient's original skin are inserted into said openings, which method comprises placing foreign skin on a carrier in a frame located within a defined system of coordinates, moving said foreign skin and carrier into predetermined positions below a first cutting means, cutting openings into said foreign skin at predetermined locations relative to each other, placing a portion of the patient's original skin on a second carrier, cutting from said portion piece having essentially the same configuration as said openings in said foreign skin, and placing said pieces of original skin into said openings in the foreign skin.

8. A method as defined in claim 7 wherein said foreign skin is cadaver skin, parts of animal skin, synthetic skin substitute, or some other skin substitute preparation.

9. A method as defined in claim 7 wherein said segments of original skin are polygonal.

* * * * *